US010160650B2

(12) United States Patent
Morris

(10) Patent No.: US 10,160,650 B2
(45) Date of Patent: Dec. 25, 2018

(54) METHOD FOR MAKING A THREE DIMENSIONAL OBJECT

(71) Applicant: Morris Brothers and Company Holdings Limited, London (GB)

(72) Inventor: Patrick John Morris, London (GB)

(73) Assignee: Morris Brothers and Company Holdings Limited, London (GB)

( * ) Notice: Subject to any disclaimer, the term of this patent is extended or adjusted under 35 U.S.C. 154(b) by 0 days.

(21) Appl. No.: 15/118,351

(22) PCT Filed: Feb. 12, 2015

(86) PCT No.: PCT/EP2015/053008
§ 371 (c)(1),
(2) Date: Aug. 11, 2016

(87) PCT Pub. No.: WO2015/121369
PCT Pub. Date: Aug. 20, 2015

(65) Prior Publication Data
US 2017/0183231 A1 Jun. 29, 2017

(30) Foreign Application Priority Data
Feb. 13, 2014 (EP) ..................................... 14155061

(51) Int. Cl.
| | | |
|---|---|---|
| *C04B 35/524* | (2006.01) | |
| *C01B 31/02* | (2006.01) | |
| *C04B 35/64* | (2006.01) | |
| *C04B 35/83* | (2006.01) | |
| *C04B 38/06* | (2006.01) | |
| *A61L 31/02* | (2006.01) | |
| *A61L 31/14* | (2006.01) | |

(52) U.S. Cl.
CPC ............ *C01B 31/02* (2013.01); *A61L 31/024* (2013.01); *A61L 31/146* (2013.01); *C04B 35/524* (2013.01); *C04B 35/64* (2013.01); *C04B 35/83* (2013.01); *C04B 38/06* (2013.01); *A61L 2430/02* (2013.01); *A61L 2430/12* (2013.01); *A61L 2430/24* (2013.01); *C04B 2235/422* (2013.01); *C04B 2235/48* (2013.01); *C04B 2235/5248* (2013.01); *C04B 2235/6567* (2013.01); *C04B 2235/665* (2013.01)

(58) Field of Classification Search
CPC ......... C04B 35/524; C04B 35/52; C08G 8/04; C08G 14/06
See application file for complete search history.

(56) References Cited

U.S. PATENT DOCUMENTS

| | | | |
|---|---|---|---|
| 4,257,405 A | 3/1981 | Colville | |
| 4,457,984 A | 6/1984 | Otani et al. | |
| 4,466,932 A * | 8/1984 | Koyama | ............... C04B 35/524 264/29.3 |
| 4,863,538 A | 9/1989 | Deckard | |
| 4,882,103 A * | 11/1989 | Kawakubo | ............ C04B 35/524 264/129 |
| 4,950,443 A * | 8/1990 | Kawakubo | ............ C04B 35/532 264/126 |
| 2003/0065400 A1 | 4/2003 | Beam et al. | |
| 2005/0079200 A1 | 4/2005 | Rathenow et al. | |
| 2006/0159718 A1 | 7/2006 | Rathenow et al. | |
| 2007/0087268 A1* | 4/2007 | Kim | ...................... H01M 4/134 429/232 |
| 2007/0202391 A1* | 8/2007 | Greiner | ............... H01M 4/8605 429/510 |
| 2008/0122141 A1* | 5/2008 | Bedal | ......................... C08J 5/00 264/405 |
| 2010/0040767 A1 | 2/2010 | Uibel et al. | |
| 2010/0325947 A1 | 12/2010 | Ohman et al. | |
| 2011/0082564 A1 | 4/2011 | Liu et al. | |
| 2011/0167530 A1* | 7/2011 | Wojtowicz | ............... B01J 20/20 2/2.5 |

FOREIGN PATENT DOCUMENTS

| | | |
|---|---|---|
| CN | 1791437 A | 6/2006 |
| CN | 102791628 A | 11/2012 |
| EP | 2537801 A1 | 12/2012 |
| EP | 2591756 A1 | 5/2013 |
| WO | 9911581 A1 | 3/1999 |
| WO | 2004087612 A1 | 10/2004 |
| WO | 2011159154 A1 | 12/2011 |
| WO | 2013144399 A1 | 10/2013 |

OTHER PUBLICATIONS

International Search Report and Written Opinion in corresponding PCT Appln. No. PCT/EP2015/053008, dated Mar. 2, 2015.
Examination Report in corresponding EP Appln. No. 14155061.6, dated Jun. 4, 2014.
Wen, Cuie, "New Titanium Alloys and Scaffolds with Ideal Biocompatibility for Biomedical Applications", http://biometal.sjtu.edu.cn/en/Show.aspx?info_lb=517&info_id=784&flag=293, Nov. 22, 2013.
Yang Zibin, "New Theory and New Technology of Current Medicines, Basic Medicines Volume, Biomedical Engineering", Heilongjiang Science and Technology Press, pp. 482-486, Jun. 30, 2000.
Office Action issued in corresponding Chinese Application No. 2015800124952, dated May 23, 2018.

* cited by examiner

*Primary Examiner* — Noah S Wiese
(74) *Attorney, Agent, or Firm* — Andrus Intellectual Property Law, LLP

(57) ABSTRACT

The present invention relates to a method for making a three dimensional carbon structure and also to a sintered article comprising pyrolyzed carbon particles. The method comprises sintering a powdered organic material, preferably using selective laser sintering, to form a sintered three dimensional structure having a desired shape. The sintered structure is then pyrolyzed to form the final carbon structure. The method is particularly useful in the production of biomedical implants such as bone scaffolds and joint replacements. In some embodiments, the powdered organic material is lignin which provides a renewable and highly cost effective starting material for the method of the present invention.

12 Claims, No Drawings

METHOD FOR MAKING A THREE DIMENSIONAL OBJECT

CROSS-REFERENCE TO RELATED APPLICATIONS

This application is the U.S. national stage application of International Application PCT/EP2015/053008, filed Feb. 12, 2015, which international application was published on Aug. 20, 2015, as International Publication WO2015/121369 in the English language. The international application is incorporated herein by reference, in entirety. The international application claims priority to EP Patent Application No. 14155061.6, filed Feb. 13, 2014, which is incorporated herein by reference, in entirety.

The invention relates to a method for making a three dimensional carbon structure and also to sintered articles comprising pyrolysed carbon particles.

BACKGROUND

Additive manufacturing (AM) is the process of producing a three-dimensional structure by building up successive layers based on a set of digital instructions. Selective laser sintering is a known method of AM which typically includes the following general steps. Powdered material such as plastic, metal, ceramic or glass is spread onto a platform and a laser is used to selectively heat an area of powdered material corresponding to a two-dimensional cross section of the final three dimensional structure. The heat from the laser causes the powdered material to fuse together. The platform is lowered and a new layer of powder is applied. The laser then selectively heats an area of powdered material corresponding to the next cross section fusing this to the cross section below. This process is repeated until the three-dimensional structure is completed. One application of additive manufacturing is for the production of porous titanium bone scaffolds for the customised medical implant market.

Traditionally, bone grafts have been used to repair damaged bone. More recently, materials such as titanium and titanium alloys have been used to produce load-bearing implants. However, titanium implants suffer from various problems. A particular problem is the stiffness of titanium relative to bone. Using Young's Modulus scale, titanium has a stiffness of 125 Gpa whereas bone has a stiffness of just 20 Gpa. Use of a titanium implant can therefore lead to "stress-shielding", meaning that the titanium implant takes the strain of weight and pressure leaving surrounding bone to weaken. This can also lead to implant loosening which is described in Wen, Cuie "Report: New titanium alloys and scaffolds with ideal biocompatibility for biomedical applications" Swinburne University of Technology, Published 2013 Nov. 18, which is herein incorporated by reference in its entirety. It is therefore desirable for bone scaffolds to have a stiffness closer to that of bone to limit or eliminate stress-shielding.

In addition, studies have shown that the release of metal ions from implant materials might have adverse biological effect or elicit allergy reaction. A current solution to this problem is careful selection of the composition of metal biomaterials to avoid or minimise adverse.

An improvement on dense metallic implants has been the use of porous scaffolds which mimic the structure of bone and allow bone tissue ingrowth, in a process known as osseointegration. Such scaffolds can be produced using "space holder" additive manufacturing methods, whereby AM is used to form a three dimensional structure comprising dispersed filler particles, and subsequently the filler particles are degraded to leave behind a porous structure. Porous structures can also be produced by foaming titanium alloy (see http://biometal.sjtu.edu.cn/en/Show.aspx?info_lb=517& info_id=784&flag=293).

Pyrolytic carbon or pyrocarbon is a synthetic substance that is generally produced by heating organic material in the absence of oxygen. It has excellent biocompatibility and hardness and is anti-thrombotic. This has led to the use of pyrolytic carbon in the production of small orthopaedic, dental and maxillofacial implants such as proximal interphalangeal (PIP) joints and bone plates.

SUMMARY OF THE INVENTION

In a first aspect, the invention provides a method of making a carbon structure, the method comprising sintering a powdered organic polymer to form a sintered first structure and pyrolysing the sintered first structure to convert it to the carbon structure.

The method of the present invention makes it possible to produce carbon structures using additive manufacturing (AM) techniques by means of a two-step process.

Firstly, a powdered fusible organic polymer is sintered to form a sintered first structure having a desired shape. Sintering may be achieved by localised heating of the fusible polymer, for example with a laser or an electron beam. Preferably, sintering is carried out in an inert atmosphere (with limited or no oxygen).

As mentioned above, laser sintering is an established technique that allows selected areas of a layer of powder to be sintered to shape without melting the whole of the powder particle layer and can be used in AM. This heating is generally achieved by controlling the speed of laser scanning (sometimes called the "dwell time") for a given laser power so that the temperature of the powder is sufficient to melt or soften at least the surface of the powder particles and allow them to fuse or sinter without causing combustion. Typically, digital instructions for producing the desired structure are implemented by a computer controlled laser based on a CAD design of the first article. The laser selectively successively sinters cross sections of the desired final three dimensional structure, incrementally building up layer upon layer of cross sections until the final three dimensional structure is complete. Methods for laser sintering are described in, for example, U.S. Pat. No. 4,863,538. The same principles apply if an electron beam rather than a laser is used to heat the powdered organic polymer.

In another embodiment, the powdered organic polymer may be sintered by heating it, for example in a mould, preferably in an inert atmosphere (with limited or no oxygen).

Whether the sintering is performed by laser, electron beam or by heating in a mould, or indeed by any other method, the sintering should generally take place between the temperature at which the particles sinter or fuse together (e.g. the melting point or softening point) of the polymer and the temperature at which it decomposes so that sintering can occur. Thus, in some embodiments, when the powdered organic polymer is heated, its particles soften and can fuse to other softened organic polymer particles at a temperature lower than the melting point of the organic polymer, assuming that it melts at all. In the case of laser sintering using AM, the sintering should occur both within a layer of powder particles and between successive layers. As described below, one of the polymers that may be used is lignin and for lignin, the polymer may be heated at a temperature of at least 130° C., at least 150° C., at least 175° C., at least 200° C., at least 225° C., at least 250° C., at least 275° C. or at least 300° C.

If the polymer is heated in a mould, it is preferably heated for at least 2 hours, at least 3 hours, at least 4 hours, at least 5 hours, at least 6 hours, at least 7 hours, at least 8 hours, at least 9 hours, at least 10 hours, at least 11 hours, at least 12 hours or at least 15 hours. The temperature and time necessary will depend on various factors, and in particular the organic polymer used, and the volume, thickness and shape of the sintered structure to be produced.

Once the sintered first structure having a desired shape has been produced, the structure is subjected to a process of pyrolysis. Pyrolysis is the thermal decomposition of organic material in the absence of oxygen. The process of pyrolysis converts the sintered organic polymer into carbon.

The carbon produced can, in some embodiments, be referred to as "pyrolysed carbon". This term is used herein to refer to a substance produced when an organic polymer undergoes pyrolysis to the extent that the percentage carbon content of the pyrolysed substance is enriched relative to the percentage carbon content of the organic polymer by causing the polymer to partly or completely decompose, leaving all or the majority of its carbon content in the second object. In some embodiments of the invention, the sintered first structure is pyrolysed to such an extent that substantially all of the sintered organic polymer is pyrolysed. Such a carbon structure may be at least 85%, at least 90%, at least 95%, at least 96%, at least 97%, at least 98%, at least 99% or 100% carbon by weight. In other embodiments, the sintered first structure is pyrolysed to an extent sufficient to produce a carbon shell or coating on some or all of the surface of the structure. For example, a core of sintered organic polymer may remain within the finished carbon structure. Alternatively, parts or regions of the first structure may be fully pyrolysed whereas other parts or regions may not be pyrolysed at all or may undergo pyrolysis sufficient to produce a coating or shell. The coating or shell may itself have a carbon content of at least 85%, at least 90%, at least 95%, at least 96%, at least 97%, at least 98%, at least 99% or 100% by weight. The thickness of the shell will depend on the dimensions and physical/technical requirements of the structure to be produced. For example, the coating or shell may have a thickness less than or equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, less than or equal to 2%, less than or equal to 1%, less than or equal to 0.5%, less than or equal to 0.1%, less than or equal to 0.05% or less than or equal to 0.01% of a maximum thickness of the structure.

The pyrolysis temperature for a given polymer will depend on the polymer used. For example, pyrolysis may be carried out at a temperature of at least 200° C., at least 300° C., at least 400° C., at least 500° C., at least 600° C., at least 700° C., at least 800° C., at least 900° C., at least 1000° C., at least 1200° C., at least 1500° C., at least 2000° C., at least 2500° C. or at least 3000° C. Pyrolysis may be carried out for at least 30 seconds, at least 1 minute, at least 5 minutes, at least 10 minutes, at least 15 minutes, at least 20 minutes, at least 30 minutes, at least 1 hour, at least 1.5 hours, at least 2 hours, at least 2.5 hours, at least 3 hours, at least 3.5 hours, or at least 4 hours. In some embodiments, pyrolysis may be carried out for a longer period of time, for example 12 hours, 24 hours or 48 hours. The temperature and time necessary will depend on various factors, and in particular the organic polymer used, the volume, thickness and shape of the sintered structure to be pyrolysed, and the degree of pyrolysis required i.e. the proportion of sintered organic polymer to be converted to carbon. Pyrolysis should be carried out in an environment substantially free from oxygen, for example in an inert atmosphere such as a nitrogen atmosphere.

It is not necessary that the pyrolysis step is conducted at a single temperature and indeed the object may be heat treated after pyrolysis is complete. In one embodiment, once a carbon structure has been produced, the method of the invention may include the additional step of heating the carbon structure at a higher temperature than the temperature used to convert the sintered first structure to carbon. This has the effect that the carbon is converted to pyrolytic carbon. Pyrolytic carbon is a material similar to graphite and has a higher strength than carbon treated at a lower temperature.

The sintering and/or pyrolysis temperature or temperatures may be programmed, for example as a staged heating cycle. In such an embodiment, the temperature may be raised at a pre-defined rate whether to a set temperature where it is held for a time before being raised to the next stage, or until it reaches a maximum temperature, after which a similar cycle of cooling may be applied to reach a base temperature, such as room temperature, in stages. A staged heating cycle may be used to control physical or chemical properties of the sintered structure and/or the final carbon structure.

Any organic polymer that can be provided in powdered form and that can be sintered and pyrolysed may be used in the present invention. The organic polymer may be a carbohydrate that can be sintered i.e. it can be provided in a powdered form that is fusible. Preferably, the organic polymer comprises or consists of lignin or a derivative or salt thereof such as lignosulphonate. The organic polymer may comprise cellulose or a derivative thereof. More than one organic polymer may be incorporated into a blend of different powdered organic polymers for sintering. Such a blend may comprise lignin at 50% or more, 60% or more, 65% or more, 70% or more, 75% or more, 80% or more, 85% or more, 90% or more, or 95% or more by weight.

An organic polymer disclosed herein, for example, lignin, a lignin derivative, cellulose or a cellulose derivative, may account for 50% or more, 60% or more, 65% or more, 70% or more, 75% or more, 80% or more, 85% or more, 90% or more, 95% or more, 96% or more, 97% or more, 98% or more, 99% or more, or 100% by weight of the total material sintered in the method of the invention.

Lignin or lignin derivatives can be obtained as by-products of commercial pulping processes. Some pulping processes, such as the sulphite process, produce lignosulphonates (lignin having sulphonate groups bonded to the lignin polymer). If a lignin derivate is used in the present invention, particular in a laser sintering method, it is preferred if the lignin derivative has a low sulphur content, preferably less than 3 mol %, less than 2 mol %, less than 1 mol %, less than 0.1 mol %, or less than 0.01 mol % sulphur. More preferably, the lignin derivative is free from sulphur e.g. it comprises no sulphonate groups or other sulphur-containing groups. Lignin with low to zero sulphur content can be obtained from other well-known pulping processes such as soda pulping ("soda lignin") and kraft pulping ("kraft lignin"). Kraft lignin may be obtained and refined using methods known in the art. For example, US2010325947 discloses a method for separating lignin from black liquor, which is a bi-product of the kraft process.

In certain methods of the invention, particularly laser sintering methods, it is preferred if the organic polymer has one or more of the following properties. Preferably, the polymer has a primary melting point of less than 200° C. The primary melting point may be from about 170° C. to about 180° C. In some embodiments, it may be preferred if the polymer has a second re-melting point about 5° C. to about 10° C. below the primary melting point, for example about 8° C. below the primary melting point. In addition, it is preferred if the difference between the softening point and the primary melting point of the polymer (delta range) is less than or equal to 10° C., more preferably less than or equal to 7° C. Furthermore, it is preferred if the polymer has a recrystallization point that is from about 50° C. lower than the primary melting point of the polymer to about 30° C. lower than the primary melting point of the polymer, preferably about 40° C. lower than the primary melting point of the polymer. The polymer may go through a melt, recrystallization, re-melt heating process.

Heating certain organic polymers can lead to the release of volatile gases. The method of the invention may include removing such gases from a chamber in which the polymer is heated during heating, or reducing or removing oxygen from the chamber to avoid combustion, for example by purging the chamber with nitrogen.

It should be noted that the sintering and/or pyrolysis steps can cause shrinkage of the structure being produced. This shrinkage can be taken into account when the AM instructions for building the structure are written or, if a mould is used, in designing the mould, such that the dimensions of the final structure meet the necessary requirements. In certain embodiments, shrinkage is advantageous. For example, it can help to "lock in" or secure any additives present in the structure. Additives that may be present in the structure are discussed in detail below.

Known AM methods allow for the production of complex structures on a variety of scales. For example, AM is currently used to produce macroscopic structures, microstructures and even nanostructures. Thus, the present invention allows for the production of carbon structures on any scale permitted by known AM methods. Moreover, the step of pyrolysis allows for the removal of organic material, allowing structures on an even smaller scale to be produced.

The organic polymer or blend of organic polymers may be mixed with or otherwise combined with (for example in a sintering powder bed) one or more additives. For example, fillers or reinforcing additives such as, for example carbon fibre, a material that will form carbon fibres at the sintering temperature and titanium may be included. As such, the method of the invention can be used to produce so called "carbon-carbon" structures. Carbon-carbon is a composite material comprising carbon reinforced with carbon fibre, and has high strength, low weight and exceptional heat resistance, making it useful in the production of, for example, heat shields and brake discs. The production of carbon-carbon may include a step of acetylene treatment, preferably following pyrolyisis.

Other additives include titanium, ceramic, glass, carbon particles or any other filler intended to remain in the final structure. In some embodiments, a degradable additive is included (for example, a sacrificial organic polymer), such that the porosity of the final structure can be controlled by adjusting the amount or type of additive. For example, the additive may comprise a material, preferably an inert material, that can be removed from the structure either during the pyrolysis step, as an additional step of the method of the invention or once the structure is "in situ". Such an additive may be soluble or may be degradable in a particular environment such as the body of a subject, by, for example, enzymatic digestion or upon exposure to an exogenous reagent.

Porosity of the final structure could also be controlled by selecting the particle size of the organic polymer prior to sintering and also controlling the degree of sintering (determined by sintering conditions such as time and temperature). In some embodiments, the powdered organic polymer is sieved prior to undergoing the sintering process in order to ensure uniformity of particle size. Preferably, particles of no more than 0.5 mm, 0.2 mm, 0.175 mm, 0.15 mm, 0.125 mm, 0.1 mm, 0.075 mm or 0.05 mm in diameter are used for the sintering process. In one embodiment, particles of no more than 0.125 mm are used. Porosity may also be controlled by adjusting the pressure under which the organic polymer is sintered, although it is not necessary to apply any external pressure during sintering and indeed during laser or electron beam sintering no external pressure is generally applied.

The distribution of particle size in the sample of powdered organic polymer to be sintered is preferably as narrow as possible. The particle size distribution (PSD) is commonly described using D values. D50 is the value of the particle diameter at 50% in the cumulative distribution (i.e. 50% of the population by volume has a diameter that is lower than this value and 50% of the population by volume has a diameter that is higher than this value). D10 is the value of the particle size at 10% in the cumulative distribution and D90 is the value of particle size at 90% in the cumulative distribution. In a preferred embodiment, the polymer sample to be sintered has the following D values:

D50=about 40 μm to about 70 μm, about 45 μm to about 65 μm or about 50 μm to about 60 μm, for example about 55 μm.

D10=about 15 μm to about 45 μm, about 20 μm to about 40 μm or about 25 μm to about 35 μm, for example about 30 μm.

D90=about 85 μm to about 115 μm, about 90 μm to about 110 μm or about 95 μm to about 105 μm, for example about 100 μm.

The mean particle diameter may be about 40 μm to about 70 μm, about 45 μm to about 65 μm or about 50 μm to about 60 μm, for example about 55 μm.

These methods of producing a porous three dimensional structure find application in the production of biomedical implants such as artificial bones or bone scaffolds as well as more generally in the fields of engineering, electronics and aerospace.

Lignin is one of the most abundant organic polymers on earth and is a waste product of the paper industry. It is therefore a renewable starting material for the method of the present invention. Another advantage of lignin is that the cost is relatively low (in the region of £2/kg). The inventor has found that powdered lignin can be sintered to form a three dimensional sintered structure which can then be pyrolysed to form a carbon structure. Thus, the present invention advantageously provides a low cost, sustainable method of making bespoke or "off the shelf" carbon structures, such as, for example, biomedical implants. By way of comparison, current biomedical implants are produced using titanium which typically costs >£50/kg and which is not renewable, or graphite which typically costs >£35/kg.

It will be appreciated that the method of the invention could be used to produce a carbon structure, a reinforced carbon-carbon structure or a pyrolytic carbon structure having any desired shape that can be produced using the sintering process outlined above. Thus, any existing structures which comprise carbon, pyrolysed carbon, pyroyltic carbon or reinforced carbon-carbon could be manufactured using the method of the present invention. Pyrolytic carbon has a wide range of applications including surgical implants, e.g. solid bone implants, such as artificial joints, or scaffolding material that is either porous or becomes porous when implanted to allow osseointegration.

Since selective sintering (for example using a laser or an electron beam) followed by pyrolysis allows for the production of a highly accurate carbon structure to be produced, the method of the invention is particularly suitable for the production of a biomedical implant which may be tailored to the specific requirements of individual patients. In one embodiment, the biomedical implant is a bone scaffold. The bone scaffold may include one or more pores which facilitate the process of osseointegration once implanted.

In other embodiments, the method of the invention may be used to produce a conventional orthopaedic implant such as a replacement joint or portion thereof, a dental implant, a maxillofacial implant or a bone plate. For example, the implant may be a proximal interphalangeal (PIP) joint implant.

In addition to its application in field of medical implants, it will be appreciated that the method of the invention can also be used in the manufacture of components or articles for the aerospace, automotive, electronics and consumer sectors, for example. In particular, the method of the invention can be used to produce, for example, heat shields, brake discs, gaskets, brake linings, brushes in electric motors, bearings, sliding elements, bushings, seals and fuel cells or any article or portion thereof where structural stability at extreme high or low temperature is a material requirement or at least beneficial.

In a second aspect, the invention provides a sintered article comprising pyrolysed carbon particles, for example a sintered article substantially composed of pyrolysed carbon particles.

The method of the first aspect of the invention can be used to produce a sintered article in accordance with the second aspect of the invention. Thus, the article may by substantially composed of pyrolysed carbon or may have a shell or coating of pyrolysed carbon surrounding or partially covering a sintered core as described in relation to the first aspect of the invention. In one embodiment, the article is made from powdered lignin or other fusible organic polymer that has been sintered and then pyrolysed.

The article may be any structure described herein, such as, for example, a biomedical implant. The implant may have specific dimensions based on the requirements of an individual patient. The implant may be a bone scaffold and/or may comprise one or more pores, which may facilitate osseointegration. In other embodiments, the implant is a conventional replacement joint or portion thereof, such as a PIP joint implant, a dental implant, a maxillofacial implant or a bone plate.

Preferred features of each aspect of the invention are as for each of the other aspects mutatis mutandis. The prior art documents mentioned herein are incorporated to the fullest extent permitted by law.

EXAMPLE 1—SINTERING OF ORGANIC POLYMERS

Materials

Two types of organic polymer powder were used for comparison: Arboform® 45 (available from Tecnaro GmbH) and Lignabond DD (available from Borregaard AS). Arboform® 45 consists largely of lignin and cellulose. Lignabond DD consists of lignosulphonate.

Preparation of Organic Polymer Powder

Both powders were sieved using 120 weight mesh resulting in particle sizes of no more than 0.125 mm in diameter.

Preparation of Airtight Container

The melting point and combustion point of Lignobond DD are within 30° C. and therefore it was decided that powder should be heated in a controlled environment in the absence of oxygen.

In order to prepare an airtight container, small tinfoil pouches were filled with organic polymer powder and sealed so that the powder formed a layer approximately 0.5 to 3 mm thick. The opening of the pouch was folded until it was tight against the powder in order to prevent oxidation as a result of exposure to free oxygen in the airspace of the container. However, the pouch provided no significant compressive force on the powder.

Sintering Method

An oven was pre-heated to 175° C. and eight airtight tinfoil pouches filled with organic polymer powder (four of each brand) were inserted and left in the ambient heat. After six hours four pouches were removed (two of each brand). After twelve hours the remaining four pouches were removed (two of each brand).

Results

All eight samples were successfully sintered (i.e. the particles of powder had fused to form a single mass). This was determined using a visual inspection. There was no significant difference between the six hour and twelve hour samples except for a darkening of the powder in the twelve hour samples. Some difference between the Arboform® 45 and Lignabond DD samples was observed. This is believed to result from additives present in Arboform® 45 which are incorporated to make it appropriate for an injection moulding process.

EXAMPLE 2—PYROLYSIS OF SINTERED ORGANIC POLYMER

Method

Four of the sintered samples produced in Example 1 (one of each brand from each duration in the sintering oven) were placed in an airtight container (this held a pocket of approx. 300 ml of air hence 370 mg of available $O_2$) and placed into an oven preheated to 200° C. for two hours.

Results

All samples pyrolysed successfully, as determined by visual inspection, and had turned to carbon. There is no discernible difference between the Arboform® 45 or Lignabond DD samples once pyrolysed.

Summary

The above Examples demonstrate that a powdered organic polymer can be sintered and pyrolysed to form a sintered, pyrolysed carbon structure. In these Examples, it was found that the powder should be housed in a controlled environment with insufficient oxygen to allow any substantial oxidation/combustion to occur. Both brands of organic polymer powder appeared to sinter equally well with no discernible difference in the carbon produced once they had gone through the process of pyrolysis. In addition, comparison of the sintered lignin powder and pyrolysed carbon with low level sintered titanium shows a very similar consistency across all three materials at this low temperature sintering point.

The invention claimed is:

1. A method of making a carbon structure, the method comprising sintering a powdered organic polymer to form a sintered first structure and pyrolysing the sintered first structure to convert it to the carbon structure, wherein the sintering step is an additive manufacturing process and wherein the powdered organic polymer comprises ligin or a salt or derivative thereof.

2. The method of claim 1, wherein the powdered organic polymer has a particle size of no more than 0.125 mm.

3. The method of claim 1, wherein an additive is included with the powdered organic polymer prior to sintering, which additive comprises at least one of: (i) a reinforcement, (ii) a filler intended to remain in the final structure, and (iii) an additive that is degradable to form pores.

4. The method of claim 3, wherein the additive is degradable and the method comprises degrading the additive to form pores in the carbon structure.

5. The method of claim 1, wherein sintering is carried out using a laser or an electron beam.

6. The method of claim 1, wherein sintering is carried out at a temperature of from 130° C. to 300° C. and/or for a period of from 2 hours to 15 hours.

7. The method of claim 1, wherein pyrolysis is carried out at a temperature of from 200° C. to 3000° C., and/or for a period of from 30 seconds to 48 hours.

8. The method of claim 1, further comprising heating the carbon structure at a temperature greater than the temperature used to convert the sintered first structure to the carbon structure, thereby producing a structure comprising pyrolytic carbon.

9. The method of claim 1, wherein the carbon structure is at least 95% carbon by weight.

10. The method of claim 1, wherein the carbon structure comprises an outer shell that is at least 95%, carbon by weight and an inner core comprising sintered organic polymer that has not undergone pyrolysis.

11. The method of claim 3 wherein the reinforcement is selected from carbon fibre, a material that will form carbon fibres at the sintering temperature, and titanium, and/or wherein the filler is selected from ceramic, glass and carbon particles.

12. A method of making a carbon structure, the method comprising sintering a powdered organic polymer to form a sintered first structure and pyrolysing the sintered first structure to convert it to the carbon structure, and heating the carbon structure at a temperature greater than the temperature used to convert the sintered first structure to the carbon structure, thereby producing a structure comprising pyrolytic carbon.

* * * * *